(12) United States Patent
Flach et al.

(10) Patent No.: US 8,571,686 B2
(45) Date of Patent: *Oct. 29, 2013

(54) FIXING FOR IMPLANTABLE ELECTRODES AND CATHETERS

(75) Inventors: Erhard Flach, Berlin (DE); Wolfgang Geistert, Rheinfelden (DE); Gernot Kolberg, Berlin (DE); Marc Kuttler, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 1134 days.

This patent is subject to a terminal disclaimer.

(21) Appl. No.: 11/185,134

(22) Filed: Jul. 20, 2005

(65) Prior Publication Data

US 2006/0020317 A1 Jan. 26, 2006

(30) Foreign Application Priority Data

Jul. 20, 2004 (DE) .......................... 10 2004 035 903
Jul. 21, 2004 (DE) .......................... 10 2004 035 987

(51) Int. Cl.
*A61N 1/375* (2006.01)

(52) U.S. Cl.
USPC ........................................................ 607/126

(58) Field of Classification Search
USPC .......................................... 607/116, 126, 128
See application file for complete search history.

(56) References Cited

U.S. PATENT DOCUMENTS

| | | | |
|---|---|---|---|
| 3,842,843 A * | 10/1974 | Mourot et al. .................. | 607/35 |
| 4,314,554 A | 2/1982 | Greatbatch | |
| 4,827,940 A | 5/1989 | Mayer et al. | |
| 5,034,186 A | 7/1991 | Shimamune et al. | |
| 5,931,864 A | 8/1999 | Chastain et al. | |
| 6,287,332 B1 | 9/2001 | Bolz et al. | |
| 6,385,491 B1 | 5/2002 | Lindemans et al. | |
| 6,473,633 B1 | 10/2002 | Heil, Jr. et al. | |
| 2002/0045926 A1 * | 4/2002 | Heil et al. ..................... | 607/116 |
| 2004/0098108 A1 * | 5/2004 | Harder et al. ................ | 623/1.15 |
| 2004/0116965 A1 * | 6/2004 | Falkenberg ........................ | 607/5 |

FOREIGN PATENT DOCUMENTS

| | | |
|---|---|---|
| DE | 300 20 200 A1 | 2/1981 |
| DE | 36 39 607 A1 | 5/1987 |
| DE | 100 48 068 A1 | 5/2001 |
| DE | 103 28 816 A1 | 1/2005 |
| EP | 0085967 A1 | 4/1983 |
| EP | 0337035 | 12/1988 |
| EP | 0 966 979 A2 | 6/1999 |
| WO | WO 2004112891 | 12/2004 |

OTHER PUBLICATIONS

CN200510087507.6 Office Action.

* cited by examiner

*Primary Examiner* — Eric D. Bertram
(74) *Attorney, Agent, or Firm* — ARC IP Law, PC; Joseph J. Mayo

(57) ABSTRACT

The invention concerns a fixing for implantable electrodes and catheters. The object of the present invention is inter alia to provide a fixing which takes account of the different demands in the course of time of ordinary use of the implantable electrodes or catheters. For that purpose the fixing includes at least one first structural element comprising a biodegradable material, namely a biodegradable magnesium alloy.

5 Claims, 5 Drawing Sheets

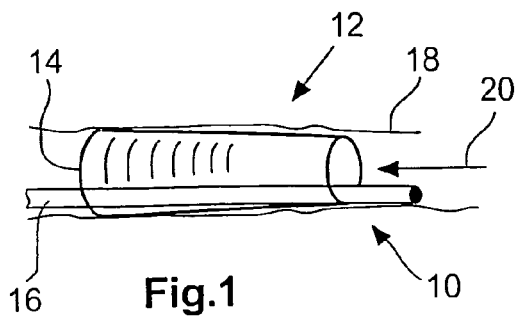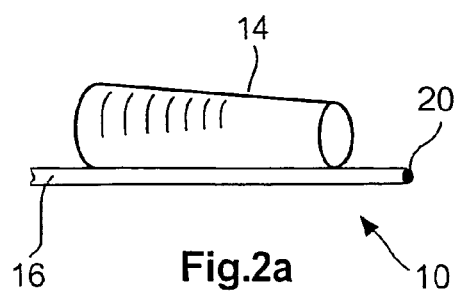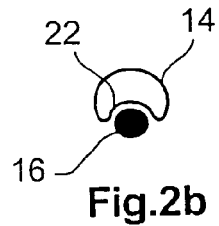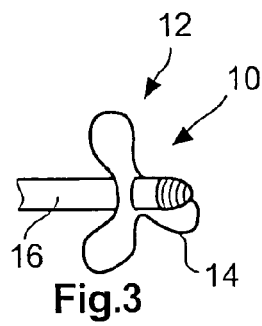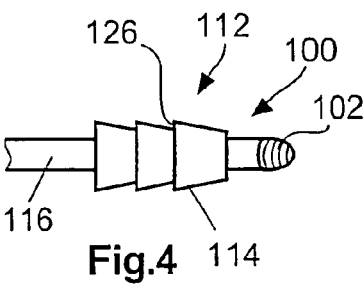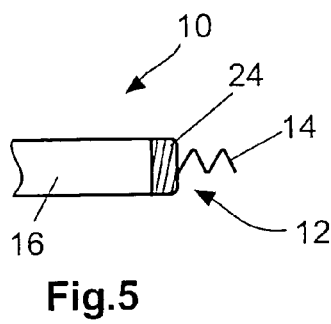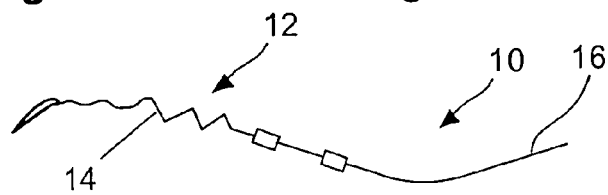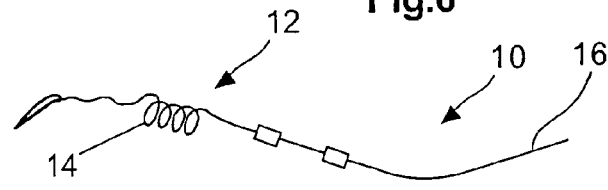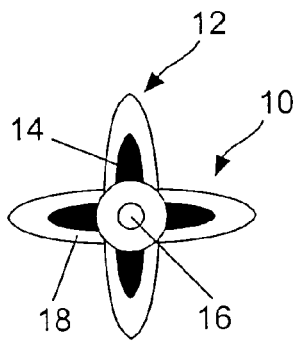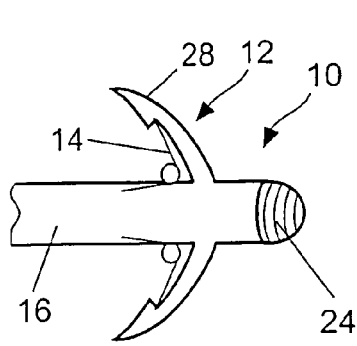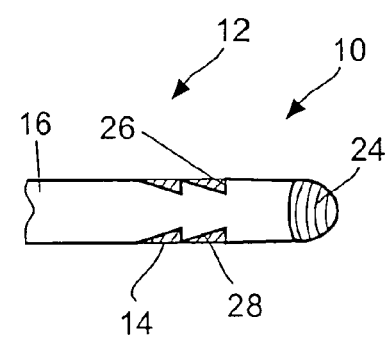

FIXING FOR IMPLANTABLE ELECTRODES AND CATHETERS

BACKGROUND OF THE INVENTION

The invention concerns a fixing for implantable electrodes and catheters.

Active electronic implants for functional electrostimulation (FES) generally have to be anchored at the location of use in order to retain their position in the tissue, which is wanted for therapy or diagnosis, over time. That is particularly important for implantable electrodes or for catheters which are fitted over a prolonged period of time and which are arranged in a moving organ matrix, for example in the heart. A large number of very different solutions have been developed for fixing purposes. Electrodes or catheters involving passive fixing (for example barb-like anchor systems consisting of the insulation material of the electrode/catheter) are distinguished from those involving active fixing (for example a screw system at the electrode head). The former are particularly suitable for anchoring in the greatly subdivided surface of the right ventricle (trabecula structure), while the latter are particularly suitable for anchoring in the smoother right atrium. All known fixings are formed from materials which are as biocompatible and bioresistant as possible (do not break down in vivo).

For use in the appropriate fashion, the electrodes/catheters are firstly positioned at the desired location in the body of the patient, anchored with suitable means and then remain in the predetermined position for a given period of time depending on the respective therapeutic or diagnostic task. After conclusion of the therapy/diagnosis or for other reasons (for example changing the battery) the electrode/catheter has to be removed again. Accordingly, very different requirements in relation to time are to be made on the fixing.

A fixing which is bulky or which already develops high levels of holding force is undesirable during positioning of the electrode/catheter as that impedes positioning and also repositioning (for the correction of defective positioning) and can result in tissue damage. That problem arises in particular in relation to passive fixings.

In addition, the holding force of the fixing changes with an increasing residence time of the implantable electrode/catheter in the body due to its gradually growing into position. Thus the holding force can still be relatively low shortly after positioning so that there is the risk of unwanted repositioning thereof. In contrast, after a prolonged residence time in the body, the electrodes/catheters can no longer be removed without major interventions for the holding forces between the fixing and the tissue environment also increase with the electrodes/catheters increasingly growing into place.

SUMMARY OF THE INVENTION

The object of the present invention is to provide a fixing which takes better account of the different demands in the passage of time in respect of regular use of the implantable electrodes or catheters.

That object is attained by the fixing according to the invention for implantable electrodes and catheters. The fixing is distinguished in that it includes at least one first structural element comprising a biodegradable material. The gradual breakdown of the first structural element makes it possible to achieve a behaviour on the part of the fixing, which is more flexible over time, for the changes caused by the breakdown also influence the holding force of the fixing. Accordingly, a further parameter for optimising the fixing properties is available to the man skilled in the art concerned with the design of fixings—an engineer with in-depth knowledge in the field of implantable medical systems. The fixing properties can be adapted depending on the respective type of electrode or catheter and the planned use.

The term 'structural element' in the sense according to the invention denotes a three-dimensional structure which forms at least a part of the fixing, which at least temporarily contributes to the level of a holding force which exists between the fixing and the surrounding tissue. The breakdown of the first structural element influences the holding force of the fixing, in which respect the 'holding force' is the force necessary to remove the electrode or the catheter in the proximal direction of the electrode line or electrical feed line again from the tissue in which it is arranged in regular use thereof. The level of the holding force is dependent on the mechanical properties of the fixing and the surrounding tissue. Accordingly, the holding force can be increased or reduced by virtue of breakdown of the first structural element, but it is also possible to compensate for a change in the holding force over time due to changes in the tissue.

A structural element can be of an active or passive nature. 'Active' means that the position and/or spatial shape of the structural element, which is necessary for the fixing effect, is adopted only due to the action of external forces. Thus, for example, during the positioning operation, a helical structural element can be screwed out of the electrode head by the surgeon by means of a screw bar and anchored in the tissue. The term 'passive structural elements' is used to denote three-dimensional structures which at least temporarily afford a hold in the tissue, by virtue of their position and/or spatial shape. Passive structural elements include for example needle-shaped, hook-shaped or anchor-shaped elements, projections (undercut configurations) on the electrode line or the catheter body and zig-zag-shaped or helical cardiac wires. Active and passive structural elements can be combined together.

The first structural element is formed from a biodegradable material. The term 'biodegradable' in accordance with the invention means a material which in a physiological environment is entirely or at least very substantially broken down by corrosive processes. In that case breakdown can be influenced inter alia by the choice of the material, application of coatings, geometry of the fixing, flow conditions in the tissue and the morphology of the material, both at the moment of initiation or complete conclusion and also in terms of its pattern in respect of time. Breakdown can occur very quickly (for example within a few minutes) or, if desired, it can also be extended over several years (for example up to ten years). The materials and also the breakdown products should be, as far as possible, biocompatible.

By virtue of the mechanical properties and the high level of biocompatibility, in accordance with the invention, there is provided the use of a biodegradable alloy based on magnesium. The proportion of the main component magnesium in the alloys is at least 50% by weight, preferably at least 70% by weight and particularly preferably at least 90% by weight. That ensures very substantial breakdown of the first structural element and very substantial resorption of the breakdown products in the body.

Particularly preferred are biodegradable magnesium alloys which contain rare earth metals and yttrium, wherein the collective term 'rare earth metal' stands for the elements scandium (atomic number 21), lanthanum (57) and the 14 elements following lanthanum, cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71) which are referred to as lanthanides. Particularly preferably, the magnesium alloys have the following proportions by weight of the alloy components:

rare earth metals between 2.0 and 5.0% by weight and/or
yttrium between 3.5 and 4.5% by weight and/or
neodymium between 1.5 and 3.0% by weight and/or
zirconium between 0.3 and 1.0% by weight and/or
aluminum <0.5% by weight, in particular <0.01% by weight and/or
balance <0.5% by weight, in particular <0.3% by weight, wherein magnesium occupies the proportion by weight that remains to 100% by weight in the alloy. The above-mentioned magnesium alloys exhibit a favourable breakdown behaviour, high biocompatibility of the alloy and also the breakdown products and they have mechanical properties which are adequate for the area of use.

In accordance with a preferred embodiment of the invention, the fixing includes a second structural element comprising a bioresistant material which forms at least a part of the fixing which at least temporarily contributes to the level of a holding force which exists between the fixing and the surrounding tissue. Accordingly, the second structural element contributes to the holding force of the fixing—whether before, during or only after breakdown of the first structural element. In that way, the fixing properties and in particular a variation in respect of time of the holding force can be predetermined by the man skilled in the relevant art in a manner which is as optimised as possible in relation to the respective requirements. Thus, for example, it can be provided that passive structural elements are present even after complete breakdown of the first structural element and afford a contribution to the holding force.

In a preferred first variant of the above-described embodiment, it is provided that the second structural element can assume at least a first and a second condition, wherein the first condition assumes a spatial shape and/or position of the second structural element, which is favourable in terms of positioning of the electrode or the catheter, and the second condition assumes a spatial shape and/or position of the second structural element, which is favourable in terms of fixing the electrode or the catheter. In addition, the second structural element is so designed that the first condition changes over into the second condition without external compulsion. The first structural element is also so designed that it fixes the first structural element in the first condition prior to initiation of the breakdown processes. The first structural element thus embraces or encloses the second structural element in such a way that it is only after breakdown or very substantial breakdown that the second condition that is wanted for the fixing can be assumed. The change from the first condition to the second condition can be achieved by mechanical prestressing but also by means of shape memory alloys. In that respect, in particular for specific conversion of the second structural element, it is possible to revert to the great variety of shapes and choice of material of known self-expanding stents.

In accordance with a second variant of a fixing which includes a bioresistant second structural element, the second structural element includes a mesh-form, grating-like or sponge-like (porous) basic structure. The first structural element can now cover that basic structure or fill the free spaces in the basic structure. With the progressive breakdown of the first structural element, that basic structure becomes accessible from the exterior, with the consequence that the surrounding tissue can grow thereinto. Accordingly the structures of the basic structure, that is to say openings, pores, recesses or the like are to be so designed in respect of their dimensions that the tissue can grow thereinto. That second variant can be implemented, for example, in such a way that a porous basic structure is predetermined as the second structural element, the pores thereof being closed with a biodegradable magnesium alloy (the filling material thus corresponds to the first structural element). With the onset of and after the conclusion of the breakdown processes, the pores are clear again and the surrounding tissue can grow into the resulting free spaces. It is however also possible for the biodegradable first structural element not to bar access for the tissue to the free spaces of the basic structure of the second structural element, but to be arranged at another location on the electrode. The process of the surrounding tissue growing into the second structural element can accordingly already begin immediately after the implantation procedure but as is known, it takes some days until that process is concluded. In that time, the contribution of the biodegradable first structural element to the holding force can prevent unwanted repositioning.

In accordance with a third variant of the fixing which includes a bioresistant second structural element, it is no longer bound directly to the electrode or the catheter. Rather, the first structural element forms a connection between the electrode or the catheter and the second structural element. Progressive breakdown of the first structural element means that the connection to the second structural element is weakened or ultimately entirely nullified. Accordingly, a proportion of the second structural element in regard to the holding force decreases in the course of time. After separation or very substantial nullification of the connection between the first and second structural elements, the electrode can be removed very much more easily and generally without complications, with the second structural element remaining in the body.

In accordance with a further preferred embodiment of the fixing according to the invention, it is provided that the fixing includes an electrical feed line which is electrically conductively connected to the first structural element and by way of which electrical voltage can be applied to the first structural element. The breakdown process can be speeded up if required by applying an electrical voltage between the feed line to the fixing and a counterpart electrode, for example, the implant housing or an electrical terminal of the electrode.

A large number of different fixing devices with fixing elements such as screws, needles, hooks, anchors (so-called tines) as well as many kinds of projections which form an undercut configuration into which tissue can grow, thereby affording a fixing, are known.

In order to be able to perform those functions those fixing elements often have sharp edges or points. Those sharp edges or points can cause unwanted injury if such an electrode or such a catheter is introduced into the body through a small orifice or through a blood vessel and is guided to the target location.

It is therefore desirable for those fixing elements to be protected for the insertion procedure by means of a temporary protective element, for example a cap. That protective element must dissolve in the body whereby the fixing elements are exposed.

Soluble caps are known for example from U.S. Pat. No. 4,827,940 and from EP 0 337 035. Those publications propose producing the caps from sugar-related materials such as mannitol, dextrose, sorbose, sucrose, or salts such as sodium chloride, potassium chloride or sodium carbonate, or from a gel-forming material such as gelatine, hydrophilic polymers, cross-linked polyethyleneglycol (PEG), cellulose, dextran and so forth.

What is common to all those materials is that they are relatively brittle or very soft so that they afford only very limited protection for the fixing elements as they could already dissolve in the insertion process. In addition it is not possible with those materials to produce a protective element which holds a fixing element which includes resilient constituents in another shape which is better suited to insertion into the body.

Therefore protective elements which—before they dissolve—protect the fixing element more effectively and/or can hold it in a form which is more suited to the insertion process would be advantageous.

A further aspect of the invention therefore involves the provision of an implantable electrode or a catheter which resolve the above-indicated problems. The fixing device is wherein the first structural element is a protective element which in the non-implanted condition embraces a second structural element serving for fixing entirely or in parts and which entirely or at least 70% by weight comprises the biodegradable magnesium alloy.

The mechanical properties of the material such as breaking strength, brittleness and modulus of elasticity as well as easy workability are particularly distinguished for the purpose of use involved. In addition, the material, as its breakdown products, exhibits a high level of biocompatibility, in part involving positive physiological effects on the surrounding tissue. Breakdown of the material takes place quickly within a few hours to days.

Preferably, the protective element consists at least 80% by weight and in particular 90% by weight of the biodegradable material. The residual constituents remaining after breakdown can no longer maintain the mechanical properties of the protective element and for the most part remain as fine powder in the body without involving serious tissue irritation. Accordingly those non-degradable constituents are to be viewed as biocompatible.

The fact of the fixing elements (of the second structural element) being embraced by the protective element, whether entirely or in parts, is to be interpreted as meaning that the partial structures of the fixing, which could cause tissue injury in the positioning procedure are covered by the protective element and can no longer interact with the surrounding tissue in an undesirable fashion. That protective embracing relationship includes the idea of the fixing also being held by the protective element in a shape which is more suitable for the positioning procedure.

In a first embodiment, such a protective element is of such a configuration that it entirely or partially embraces the second structural elements necessary for fixing, in particular points, edges or projections, so that they are no longer exposed and could not unintentionally damage the tissue in the positioning operation.

In a second embodiment the protective element holds the second structural elements of the fixing, which are necessary for fixing purposes, in a shape which is more favourable for the insertion procedure. As soon as the protective element is broken down the second structural element changes into a second shape which is more favourable for fixing in the surrounding tissue.

Such a protective element can comprise a relatively thin wall which encloses a cavity. Such a protective element however, can also comprise solid material or foamed material, in which the second structural element is embedded. Finally, such a protective element can also comprise a wire or strip construction which is of a relatively open configuration. The protective element can assume the form of a cap, a clip or a ring in order to protect the second structural element.

BRIEF DESCRIPTION OF THE SEVERAL VIEWS OF THE DRAWINGS

The invention is described in greater detail hereinafter by means of embodiments by way of example with reference to the accompanying drawings in which:

FIG. 1 shows a view of an electrode in the region of a fixing which includes an expandable structural element, FIGS. 2a and 2b show a view of and a cross-section through an electrode in the region of a fixing in which the electrode is secured to the outside periphery of an expandable structural element, FIG. 3 shows a view of an electrode in the region of a fixing which includes a structural element in the form of a fixing anchor, FIG. 4 shows a view of a catheter in the region of a fixing which includes a cylindrical-sawtooth-shaped structural element, FIG. 5 shows a view of an electrode in the region of a fixing which includes a structural element in the form of a helical coil, FIG. 6 shows a view of an electrode in the region of a fixing which includes a structural element in the form of a zig-zag-shaped cardiac wire, FIG. 7 shows a view of an electrode in the region of a fixing which includes a structural element in the form of a helical cardiac wire, FIG. 8 is a rear view on to a cross-section through an electrode beneath the fixing which includes a structural element in the form of a fixing anchor, FIG. 9 shows a longitudinal section through an electrode in the region of a fixing which includes a structural element in the form of a fixing anchor, FIG. 10 shows a longitudinal section through an electrode in the region of a fixing which includes a cylindrical-sawtooth-shaped structural element.

DETAILED DESCRIPTION OF THE INVENTION

Figure 11A:
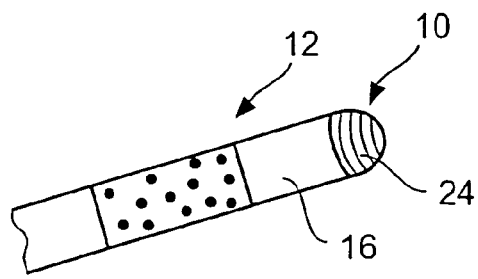
FIGS. 11a and 11b show a view of and a longitudinal section through an electrode in the region of a fixing which includes a porous basic body as a structural element.

Fixings according to the invention are described in a wide range of different configurations hereinafter, in a number of embodiments by way of example. The scope of protection of the claims however is not to be limited to the specific embodiments by way of example, but rather they serve only to illustrate the idea of the invention. What is common to the fixings according to the invention is that they include at least one first structural element comprising a biodegradable material, more specifically a biodegradable magnesium alloy with the following proportions by weight:

| | |
|---|---|
| rare earth metals | 2.0-5.0% by weight and |
| yttrium | 3.5-4.5% by weight and |
| neodymium | 1.5-3.0% by weight and |
| zirconium | 0.3-1.0% by weight and |
| aluminum | <0.01% by weight and |
| balance | <0.3% by weight, | wherein magnesium forms the proportion that remains to 100% by weight in the alloy. The stated magnesium alloy has material properties which are particularly suitable for implementation of the fixings described hereinafter in the embodiments by way of example. In addition, the alloy and also the breakdown products thereof exhibit a high level of biocompatibility. Furthermore the breakdown products or the breakdown processes in vivo appear to exert a positive physiological effect on the surrounding tissue so that rejection reactions are at least alleviated. All embodiments described hereinafter by way of example can be produced on the basis of the above-mentioned magnesium alloy. It is however, also possible for the alternative biodegradable materials described further hereinbefore to be used in combination or in supplementary relationship. What is common to all materials used for implementation of the first structural element is that they are broken down in vivo. Accordingly, a contribution on the part of the first structural element to the holding force of the fixing changes with time.

FIG. 1 is a diagrammatic view showing a portion of an electrode 10, more specifically in the region of the distal end of the electrode line 16 in which the fixing 12 is arranged. The fixing 12 includes a tubular first structural element 14 which is formed from the biodegradable material. The first structural element 14 can assume a first condition in which it is of a smaller cross-section which is thus more favourable in terms of positioning in the body of the patient. At the implantation location, the first structural element 14 is changed into a second condition by expansion. For that purpose, the fixing 12 includes expansion means—not shown in detail here—such as, for example, an inflatable balloon disposed on the electrode line 16. The specific construction of the first structural element 14 and also of the expansion means can be based on per se known solutions which have been developed in the field of implantable vessel supports (stents). In the expanded second condition, the first structural element 14 bears against the vessel walls 18 which are diagrammatically indicated here and thus contributes to the holding force of the fixing 12. The term holding force is used to denote the force necessary to remove the electrode 10 again in the proximal direction of the electrode line 16 (indicated by the arrow 20). It will be appreciated that, with increasing breakdown of the first structural element 14, the contribution thereof to the holding force decreases. On the other hand the electrode 10 simultaneously grows into the surrounding tissue so that its contribution to the holding force increases.

In the fixing shown in FIG. 1, the electrode 10 with the electrode line 16 is disposed in the interior of the expandable first structural element 14. Alternatively, it is possible to adopt an arrangement as shown in FIGS. 2*a* and 2*b* in which the electrode line 16 is arranged at the outside periphery of the first structural element 14, in particular in a semicircular elongate recess 22 provided for that purpose. Upon expansion of the first structural element 14, which is of a similar design configuration to FIG. 1, the electrode line 16 together with the electrode head 24 is pressed against the vessel wall.

FIG. 3 shows an electrode 10 in the region of its fixing 12. The fixing 12 includes a first structural element 14 which assumes the shape of a fixing anchor made from a wire of the biodegradable material.

FIG. 4 shows an end region of a catheter 100 which carries an electrode head 102 and a fixing 112. The fixing 112 includes a first structural element 114 comprising the biodegradable material, which is of a cylindrical-sawtooth-shaped contour forming undercut configurations 112 in the proximal direction of an electrical feed line 116 of the catheter 100.

FIG. 5 shows a distal end of an electrode line 16 of an electrode 10, which includes an active fixing 12. Active means that the position of the first structural element 14, which is necessary for the fixing action, is only assumed by virtue of the action of external forces. Specifically, in the present case a screw bar—not shown here—is passed by way of a lumen in the electrode line 16 to the rear side of the fixing 12 and there engages into complementary structures—also not shown. By rotation of the screw bar, the first structural element 14 is unscrewed from the electrode head 24 and anchored in the adjoining tissue. The first structural element 14 which is in the form of a helical coil comprises the biodegradable material.

FIGS. 6 and 7 diagrammatically show two different embodiments of two cardiac electrodes 10, in each case once again in a portion thereof which illustrates a distal end of the electrode line 16 with fixing 12. As can be seen, the fixing 12 of both embodiments includes passive first structural elements 14 in the form of a so-called cardiac wire. In the embodiment shown in FIG. 6 that cardiac wire is of a zig-zag configuration while in the embodiment shown in FIG. 6 it is of a helical configuration. The first structural element 14 is formed from the biodegradable material.

FIG. 8 provides a rear view on to the distal end of an electrode 10, more specifically along a section through the electrode line 10 just beneath the fixing 12. It includes anchor-shaped first and second structural elements 14, 28. The second structure 28 is formed from a bioresistant material, for example the insulation material of the electrode line 16. In some portions, the anchor-shaped second structural element 28 is connected or coated with a biodegradable first structural element 14 for reinforcement purposes. By virtue of gradual breakdown of the first structural element 14 after implantation of the electrode 10, a contribution on the part of the structural elements 14, 28 to the holding force is reduced, for their mechanical resistance to displacement in the proximal direction of the electrode line 16 will fall with increasing material breakdown.

FIG. 9 shows a longitudinal section through an electrode 10 with a further alternative embodiment of its fixing 12. The fixing 12 again consists of a first structural element 14 comprising the biodegradable material and a second structural element 28 comprising a bioresistant material. The second structural element 28 forms an anchor-shaped structure which is reinforced on its side towards the electrode line 16 by the first structural element 14. The first structural element 14 is a biodegradable wire which is supported at predetermined locations of the second structural element 28 or the electrode line and thus contributes to the holding force. The second structural element 28 can be formed for example from the insulation material of the electrode line 16, in general a silicone. When the first structural element 14 is at least very substantially broken down, a mechanical resistance of the fixing 12 to displacement in the proximal direction of the electrode line 16 falls.

The electrode 10 in FIG. 10 has a fixing 12 with cylindrical-sawtooth-shaped second structural elements 28 which form undercut configurations 26 in the direction of the proximal end of the electrode 10. The cylindrical-sawtooth-shaped recesses of the second structural element 28 are filled with a first structural element 14 which is of a complementary contour and which comprises the biodegradable material. During and after breakdown of the first structural element 14 the surrounding tissue grows into the resulting free spaces so that the holding force is generally increased.

Figure 11B:
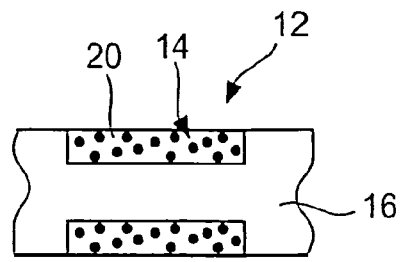

FIGS. 11*a* and 11*b* show a view on to and a longitudinal section through a distal portion of an electrode 10 with a fixing 12. It is of a sleeve-shaped contour and is disposed in a peripherally extending recess which is complementary thereto in the insulating material of the electrode line 16. The fixing 12 is composed of a first and a second structural element 14, 28. The second structural element 28 includes a rigid, bioresistant basic structure having a plurality of pores. Those pores are filled with the first structural element 14 comprising a biodegradable material prior to implantation. The first structural element 14 is broken down in the body and the surrounding tissue can grow into the pores which are then exposed. The dimensions of the pores are predetermined accordingly.

Figure 12:
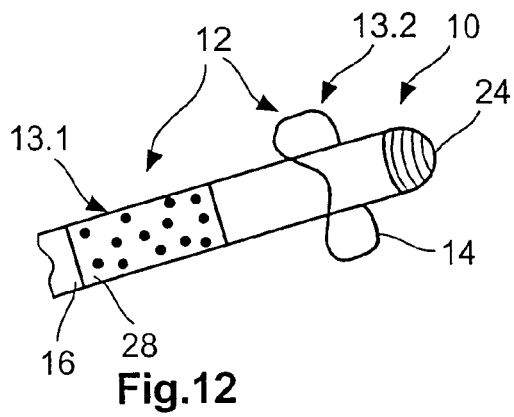
FIG. 12 shows a view of an electrode in the region of a fixing which includes a structural element in the form of a fixing anchor and a porous basic body.

FIG. 12 shows an electrode 10 whose fixing 12 uses a combination of the first and second structural elements 14, 28 shown in FIGS. 11*a* and 11*b* and FIG. 3. A proximally disposed portion 13.1 of the fixing 12 includes a second structural element 28 which is formed from a bioresistant material and which forms a basic structure like that shown in FIGS. 11*a* and 11*b*. In that respect, attention is directed to the description relating thereto. The fixing 12 further includes a distal portion 13.2 with an anchor-shaped first structural element 14 comprising the biodegradable material. While the surrounding tissue is growing into the basic structure of the second structural element 28 the first structural element 14 contributes substantially to the holding force. After breakdown thereof, the electrode 10 can be removed in the proximal direction without serious complications because of the more favourable isodiametric shape of the second structural element 28.

Figure 13:
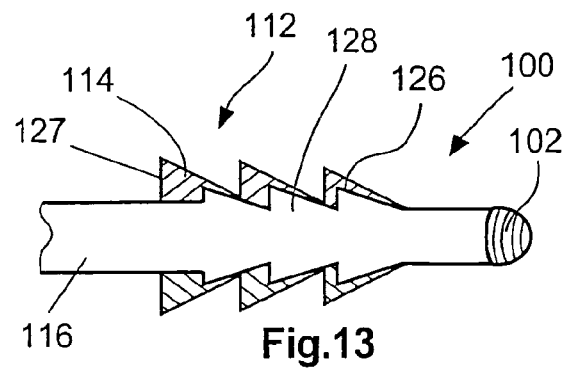
FIG. 13 shows a longitudinal section through a catheter in the region of a fixing which includes a cylindrical-sawtooth-shaped structural element.

FIG. 13 shows a longitudinal section through a catheter 100 in the region of a fixing 112 which includes a biodegradable first structural element 114 and a bioresistant second structural element 128. Both structural elements 114, 128 are of a cylindrical-sawtooth-shaped contour which forms undercut configurations 126 and 127 respectively in the proximal direction of the electrical feed line 116 of the catheter 100. The undercut configurations 126 of the second structural element 128 are smaller in their dimensions than the undercut configurations 127 of the first structural element 114. Accordingly the contribution of the fixing 112 to the holding force will decrease in the course of time.

Figure 14:
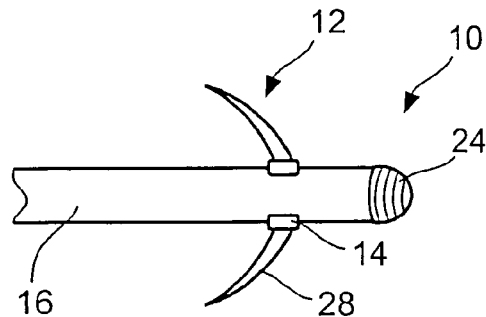
FIG. 14 shows a longitudinal section through an electrode in the region of a fixing which includes a structural element in the form of a fixing anchor which adheres by way of a connection to the electrode body.

FIG. 14 is a longitudinal section through an electrode 10 in the region of a fixing 12, in which the first structural element 14 is formed from a biodegradable material and acts as a connection to a bioresistant second structural element 28. After breakdown of the first structural element 14, the anchor-shaped second structural element 28 remains in the body when the electrode 10 is removed.

Figure 15A:
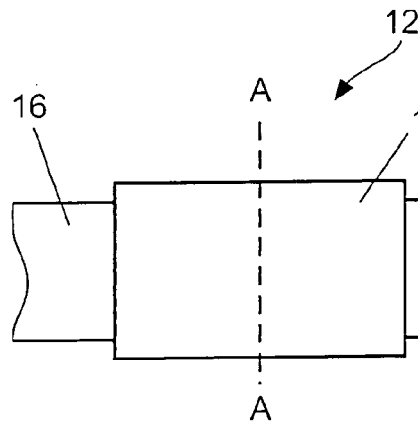
FIGS. 15a and 15b show a view of and a cross-section through an electrode in the region of a fixing which includes an expandable structural element.
Figure 15B:
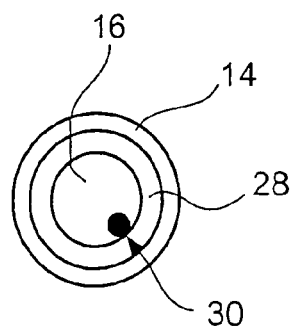

Finally FIGS. 15*a* and 15*b* show a further alternative variant of an electrode 10 with a fixing 12 in a view on to the portion of the electrode 10 carrying the fixing 12 and in an associated cross-section along line A-A respectively. As can be seen from FIG. 15*b* the fixing 12 is composed of two tubular first and second structural elements 14, 28. The first structural element 14 is formed from the biodegradable material and is so designed that it holds in a first condition, the second structural element 28 which is formed from a bioresistant material. Accordingly, the second structural element 28 can assume a first condition in which it is of a smaller cross-section and is thus of a contour which is more favourable for the positioning procedure. In addition the second structural element 28 is designed in such a way that it can enlarge in a self-expanding mode, that is to say without external compulsion, from the first condition into at least one second condition. Structures of that kind can be borrowed from known medical support implants from the endovascular sector (stents). After (substantial) breakdown of the first structural element 14 in the body, the second structural element automatically expands. That process can be accelerated by applying a voltage by way of an electrical feed line 30 which is electrically connected to the first structural element 14 by way of the second structural element 28, that voltage causing galvanic decomposition of the first structural element 14. The electrode head 24 can serve as the counterpart electrode.

Figure 16:
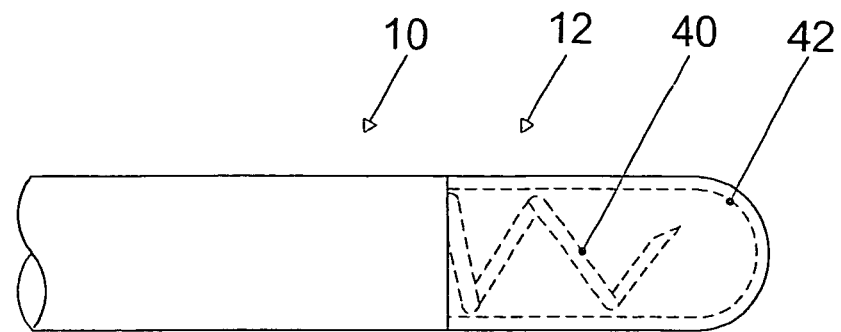
FIG. 16 shows the tip of an electrode with a fixing including a protective element.

FIG. 16 shows the tip of an electrode 10 with a fixing device 12. The fixing 12 includes a screw helix as a structural element of the fixing (corresponds to the second structural element, formed from a bioresistant material, of the foregoing examples; referred to and in the following examples as the fixing element 40) and a hollow cap as a protective element 42, in which respect the fixing element 40 is enclosed by the cap in such a way that atraumatic insertion through a vessel or through a small orifice is possible. The protective element 42 comprises a biodegradable magnesium alloy of the above-specified composition which dissolves in the body and thus exposes the fixing element 40 (the protective element 42 corresponds here and in the following examples to the first structural element of the preceding examples).

Figure 17:
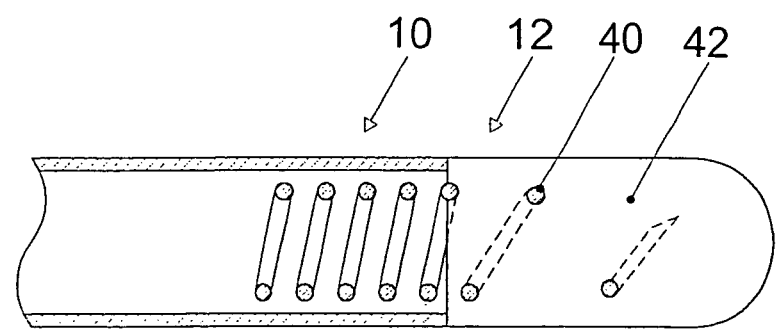
FIG. 17 shows the tip of an electrode with a fixing including a protective element, in accordance with a second alternative.

FIG. 17 shows a longitudinal section through the tip of an electrode 10 with a fixing device 12, in which there is provided a screw helix as the fixing element 40 and in which that fixing element 40 is embedded completely into a biodegradable material of a magnesium alloy which assumes the shape of a cap and serves as the protective element 42.

Figure 18A:
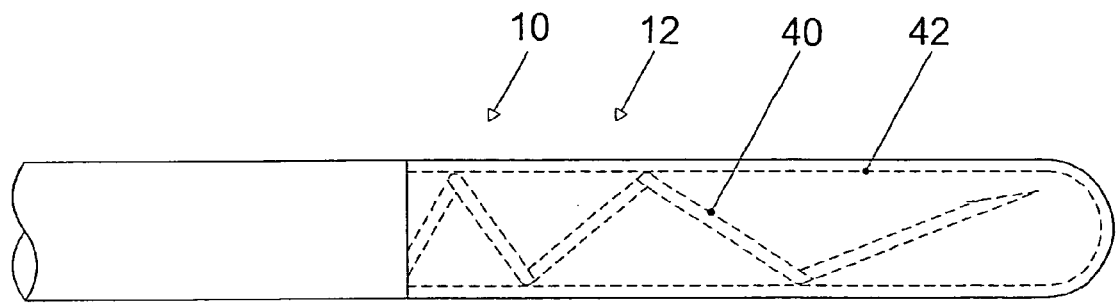
FIGS. 18a and 18b shows the tip of an electrode with a fixing including a protective element, in a third alternative.
Figure 18B:
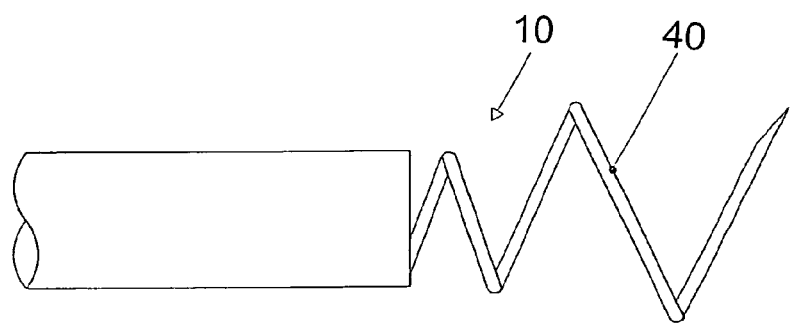

FIG. 18*a* shows the tip of an electrode 10 with a fixing device 12, in which there is provided a screw helix as the fixing element 40, wherein the screw helix is held by a cap as the protective element 42 in a first shape whose diameter is smaller than a diameter of the screw helix in a relieved second shape. In other words, the fixing element 40 firstly assumes a first shape which is more favourable for the insertion procedure. As soon as the cap is broken down, the fixing element changes into the second shape which is better suited for fixing in the surrounding tissue. FIG. 18*b* shows the same arrangement after the protective element 42 has dissolved.

Figure 19A:
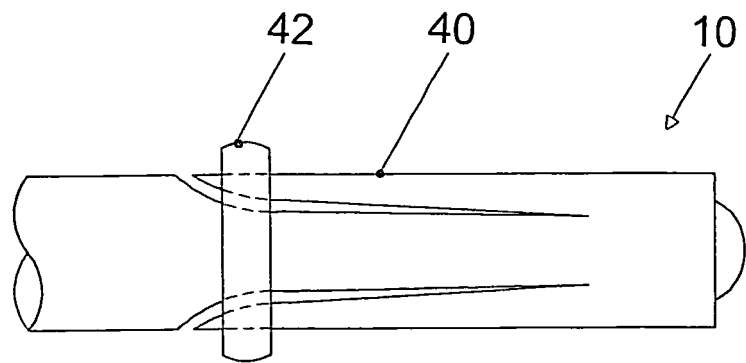
FIGS. 19a and 19b shows the tip of an electrode with a fixing including a protective element, in a fourth alternative.
Figure 19B:
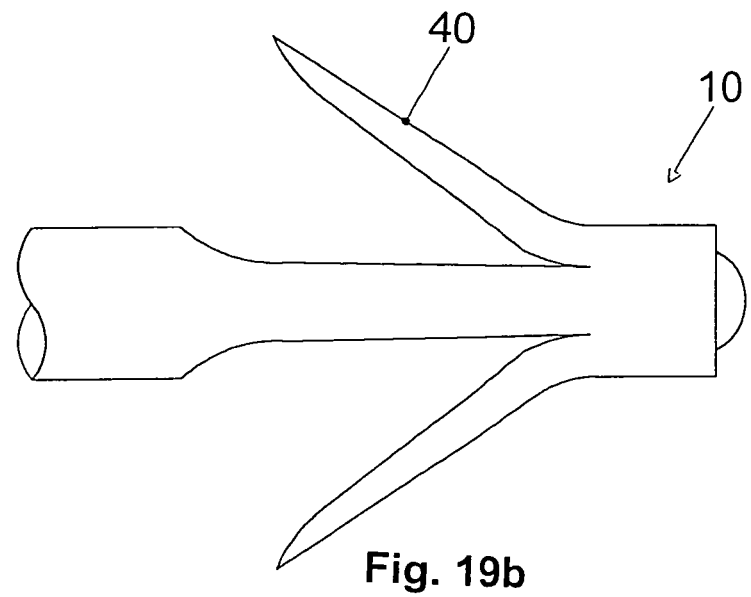

FIG. 19*a* shows the tip of an electrode 10, in which there are provided anchors as the fixing elements 40 which can be deployed by a resilient component or by inherent spring properties, that is to say which can change from a first shape which is more favourable for the positioning operation, into a second shape which is more favourable for the fixing action when the protective element 42 which is in the form of a band or strip has dissolved. FIG. 19*b* shows the same arrangement after the protective element 42 has dissolved.

What is claimed is:

1. An implantable electrode comprising
an electrode line having a proximal end and a distal end,
wherein said electrode line comprises an electrode head and a fixing situated near, but proximal to, said distal end,
wherein the fixing includes
at least one first structural element having a spatial shape that affords a hold in tissue and maintains electrical contact between the electrode and the tissue in a deployed state;
wherein the at least one first structural element comprises a biodegradable material, and wherein the material includes a magnesium-based biodegradable alloy;
wherein said electrode line further comprises a central axis and wherein the at least one first structural element extends radially outward from said central axis; and
wherein said at least one first structural element comprises a holding force such that said holding force decreases over time when said biodegradable material exhibits gradual breakdown;
wherein the fixing further includes
a second structural element of a bioresistant material, configured as at least a part of the fixing which at least temporarily contributes to a level of a holding force inch exists between the fixing and the tissue; and,
wherein the second structural element includes
a mesh-form or
grating-like or
sponge-like basic structure
having a plurality of pores;
wherein said second structural element comprises said biodegradable material situated in said plurality of pores;
wherein said plurality of pores extend radially inward toward said central axis of said electrode line; and,
wherein said holding force of said second structural element comprising said biodegradable material situated in said plurality of pores increases over time when said biodegradable material in said plurality of pores exhibits gradual breakdown, such that one or more of said plurality of pores are cleared enabling the tissue to row into the cleared one or more plurality of pores.

2. The implantable electrode as set forth in claim 1, wherein the alloy is a magnesium alloy which contains rare earth metals and yttrium.

3. The implantable electrode as set forth in claim 1, wherein the alloy is a magnesium alloy with proportions by weight of alloy components selected from the group consisting of:
rare earth metals between 2.0 and 5.0% by weight;
yttrium between 3.5 and 4.5% by weight;
neodymium between 1.5 and 3.0% by weight;
zirconium between 0.3 and 1.0% by weight;
aluminum 0.5% by weight;
balance 0.5% by weight and combinations thereof;
wherein magnesium occupies the proportion by weight that remains to 100% in the alloy.

4. The implantable electrode as set forth in claim 1, wherein the at least one first structural element includes a wire.

5. The implantable electrode as set forth in claim 1, wherein the at least one first structural element includes a wire, and wherein the wire comprises the biodegradable material and is configured in a shape of a fixing anchor.

* * * * *